(12) United States Patent
Thompson et al.

(10) Patent No.: US 9,956,145 B2
(45) Date of Patent: May 1, 2018

(54) VISUAL COUNTING SYSTEM

(71) Applicants: Derek William Thompson, Knightdale, NC (US); Brian Marshall Burney, Wake Forest, NC (US); Bryant James Deakins, Raleigh, NC (US); Corey Spencer Martin, Raleigh, NC (US); Michael Jones, Raleigh, NC (US); Steven Craig Israel, Durham, NC (US)

(72) Inventors: Derek William Thompson, Knightdale, NC (US); Brian Marshall Burney, Wake Forest, NC (US); Bryant James Deakins, Raleigh, NC (US); Corey Spencer Martin, Raleigh, NC (US); Michael Jones, Raleigh, NC (US); Steven Craig Israel, Durham, NC (US)

( * ) Notice: Subject to any disclaimer, the term of this patent is extended or adjusted under 35 U.S.C. 154(b) by 17 days.

(21) Appl. No.: 14/862,544

(22) Filed: Sep. 23, 2015

(65) Prior Publication Data

US 2017/0079885 A1    Mar. 23, 2017

(51) Int. Cl.
*A61J 7/02*         (2006.01)
*H04N 5/225*        (2006.01)
*H04N 5/33*         (2006.01)
*G06M 11/00*        (2006.01)
*G06M 1/02*         (2006.01)
*G06K 9/00*         (2006.01)

(52) U.S. Cl.
CPC .................. *A61J 7/02* (2013.01); *G06K 9/00* (2013.01); *G06M 1/022* (2013.01); *G06M 11/00* (2013.01); *H04N 5/2252* (2013.01); *H04N 5/2256* (2013.01); *H04N 5/33* (2013.01)

(58) Field of Classification Search
None
See application file for complete search history.

(56) References Cited

U.S. PATENT DOCUMENTS

| 6,177,683 | B1 * | 1/2001 | Kolesar | .............. | G06K 7/10722 |
| | | | | | 235/468 |
| 6,574,580 | B2 | 6/2003 | Hamilton | | |
| 6,610,973 | B1 * | 8/2003 | Davis, III | ................. | A61J 7/02 |
| | | | | | 250/222.1 |
| 6,738,723 | B2 | 5/2004 | Hamilton | | |

(Continued)

FOREIGN PATENT DOCUMENTS

WO    WO 0225568 A2 *  3/2002   ........... G06F 19/326
WO    WO2014065872     5/2014

*Primary Examiner* — Vu Le
*Assistant Examiner* — Tracy Mangialaschi
(74) *Attorney, Agent, or Firm* — Southeast IP Group, LLC.; Thomas L. Moses

(57) ABSTRACT

A low-profile visual counting system is provided and designed to count pills or other small discrete objects. This technology is vision based, which allows a pharmacist or other user to pour pills onto a counting surface in a single layer, and then the device tells the user how many pills are on that surface. The present device places the camera and preferably an infrared light source below the counting surface. This offers the unique advantage of not having to mount a camera above the counting surface which reduces the size and improves the aesthetic characteristics of such a device. The image is captured and then processed to determine the number of pills on the surface. This system may be interfaced with other networks, terminals, and existing pharmacy management systems.

17 Claims, 5 Drawing Sheets

(56) References Cited

U.S. PATENT DOCUMENTS

| | | |
|---|---|---|
| 6,771,369 B2 | 8/2004 | Rzasa et al. |
| 7,006,214 B2 | 2/2006 | Rzasa et al. |
| 7,028,723 B1 | 4/2006 | Alouani et al. |
| 7,317,525 B2 | 1/2008 | Rzasa et al. |
| 7,391,898 B2 | 6/2008 | Macy et al. |
| 7,570,786 B2 | 8/2009 | Ateya |
| 7,599,516 B2 | 10/2009 | Limer et al. |
| 8,215,557 B1 | 7/2012 | Reno et al. |
| 8,374,965 B2 | 2/2013 | Friend et al. |
| 8,457,384 B2 | 6/2013 | Smilansky |
| 8,712,163 B1 | 4/2014 | Osheroff |
| 8,861,816 B2 | 10/2014 | Lang et al. |
| 9,116,887 B2 | 8/2015 | Botten |
| 2007/0189597 A1* | 8/2007 | Limer ..................... A61J 7/02 382/153 |
| 2012/0201434 A1* | 8/2012 | Natali ................ G01N 21/9508 382/128 |
| 2013/0058550 A1* | 3/2013 | Tanimoto ........... G01N 21/9508 382/128 |
| 2013/0141566 A1* | 6/2013 | Lang .................... G06K 9/3241 348/135 |
| 2013/0142406 A1* | 6/2013 | Lang .................... G06K 9/6293 382/128 |

* cited by examiner

VISUAL COUNTING SYSTEM

BACKGROUND OF THE INVENTION

Pill counting in pharmacies is necessary for the filling of prescriptions. Heretofore, this counting process involved a pharmacist or other qualified pharmacy employee pouring out a quantity of pills or capsules from a supply container and manually counting the required number of pills. The excess units are then returned to the supply bottle, while the proper number of counted units is poured into a vial to be presented to the patient for whom the prescription was written.

More recently, a variety of devices have been developed and utilized to count pills or capsules automatically, thus eliminating or reducing the need for manual counting. These devices also serve to decrease human error and improve counting accuracy. Such devices, however, typically utilize complex mechanisms and complex electronic control. This complexity tends to drive up the cost of automated pill counters, making them expensive to build, purchase, and maintain.

While most pill counting devices involve substantial complexity and cost, an alternative approach has been described in the recent art that provides automated counting with greatly reduced electromechanical complexity and cost. This approach utilizes digital image capture means to provide suitably programmed image processing means with information sufficient to count the number of pills present within the area imaged by the digital image capture device.

Current commercially available pill counting systems include Kirby Lester's KL1, KL1plus, KL15e, KL20, and KL30, Avery Weightronix's Eyecon, Innovation's Optix. The Kirby Lester products require the user to pour the pills through a funnel and the pills are counted as they break the beam of a counting sensor. The Eyecon and Optix products use a camera to capture an image of the pills on a tray in order to determine the number of pills.

The following patents and publications describe prior art pill counting systems and are incorporated herein by reference.

U.S. Publication No. US2013/0221082 describes an apparatus for identifying a medicinal substance. A tray receives and concurrently supports a plurality of pills formed at least in part from the medicinal substance. A computer-readable memory stores a drug database including one or more identifying features for identifying different pills formed at least in part from different medicinal substances. A recognition device is arranged to interrogate the pills on the tray and detect at least one of the identifying features from the pills. A controller receives the identifying feature(s) detected by the recognition device and determines the identity of the medicinal substance from among the different medicinal substances in the drug database based on the identifying feature(s).

International Publication No. WO2014/065872 describes embodiments of work stations for use in medical dose preparation management system. A work station may include a camera stand. The camera stand may include a housing enclosing a camera and one or more light sources therein. As such, the camera and light sources may be directed at a medical dose preparation staging region to capture medical dose preparation images of the medical dose preparation staging region. The camera stand may include an adjustable support positionable in a plurality of positions to dispose the camera and light source relative to the medical dose preparation staging region. A base with a removable tray may be provided that include medical receptacle engagement features. The work stations may facilitate improved image quality, efficiency of work flows carried out at the work station, and administrative tasks such as cleaning.

U.S. Pat. No. 8,457,384 describes a universal counting and measurement system and method. The system and method are not restricted to a specific application, aimed at counting a specific type of object, but are capable of counting objects of a large variety of sizes and shapes. According to certain embodiments, the system and method are also capable of measuring volumes of materials held within a container or piled on a surface. The shape of the containers or the shape of the pile of material are not limited to a certain prescribed architecture. According to certain embodiments, the system is easily adapted to the different applications and can be made ready to work in a short time. The system is also capable of counting accumulating objects or measuring accumulating volumes within one or more containers or piles.

U.S. Pat. No. 8,712,163 describes a computer-implemented method of pill analysis including the steps of acquiring a pill image having an image frame and detecting contrast shifts within the image frame to locate at least one object with an object outline. A first value for the object(s) is determined, where the value is an area, a position, a length, a width, an angle, a color, a brightness, a code, a shape, a crystal pile size, a crystal geometry, a substance identity, or a character identity. Based on the first and second values, the computer outputs a result to a user.

U.S. Publication No. US2013/0142406 describes a method of processing graphical image data representing optically scanned medication-related units may include receiving image data generated responsive to disposal of the units on a tray disposed a distance from an image acquisition component, the image data including data indicative of visually observable features of the units disposed on the tray. The method further includes comparing at least two features among the visually observable features from the image data to reference data indicative of corresponding features of reference units. The reference data is selected for comparison based on an identification of the reference data as corresponding to a prescription being processed. The reference data includes data indicative of features of the reference units extracted from images captured using hardware corresponding to hardware used to generate the image data. The method further includes generating a likelihood rating for each of the at least two features based on the comparing.

BRIEF SUMMARY OF THE INVENTION

The visual counting system of the present invention is a low profile, countertop device designed to count pills or other small discrete objects. The intended application is for use in pharmacies to facilitate counting pills when filling prescriptions. The present invention is a vision based counting technology, preferably including an infrared light source and a camera operatively connected to a computer, which allows a pharmacist or other user to pour pills onto a counting surface in a single layer, and then the device tells the user how many pills are on that surface. The pharmacist then removes the pills from the counting surface and places them into the medicine vial.

The present visual counting system is different from existing counting technologies currently on the market. Existing vision based counting solutions contain a backlit counting surface with camera on the opposite side, typically mounted above the counting surface. The present device places the camera and preferably an infrared light source below the counting surface. This offers the unique advantage of not having to mount a camera above the counting surface which reduces the size and improves the aesthetic characteristics of such a device. In a preferred embodiment, the camera does not contain an IR filter commonly found on most standard cameras. The counting surface preferably consists of a dark colored IR transmissive material optionally covered by a protective layer of glass. The dark color reduces background noise, and the IR transmissive material allows the IR illumination to pass through and reflect off of the bottom side of the pills back to the camera. The image is captured and then processed to determine the number of pills on the surface. Other wavelengths of light may also work with the appropriate supporting hardware (camera, counting surface, and light source).

The core of the technology is the camera and light setup; however, this can be implemented in any number of final embodiments. The device can have a simple display that only shows the number of pills on the counting surface, or it can have a fully functional display screen that can display the image, workflow features, inventory functions, networking and setup utilities, etc. The image of the pills can be saved, transmitted or printed if deemed appropriate features for a final product.

DESCRIPTION OF THE DRAWINGS

These and other features, aspects, and advantages of the present invention will become better understood with regard to the following description, appended claims, and accompanying drawings where:

DETAILED DESCRIPTION OF THE INVENTION

Figure 1:
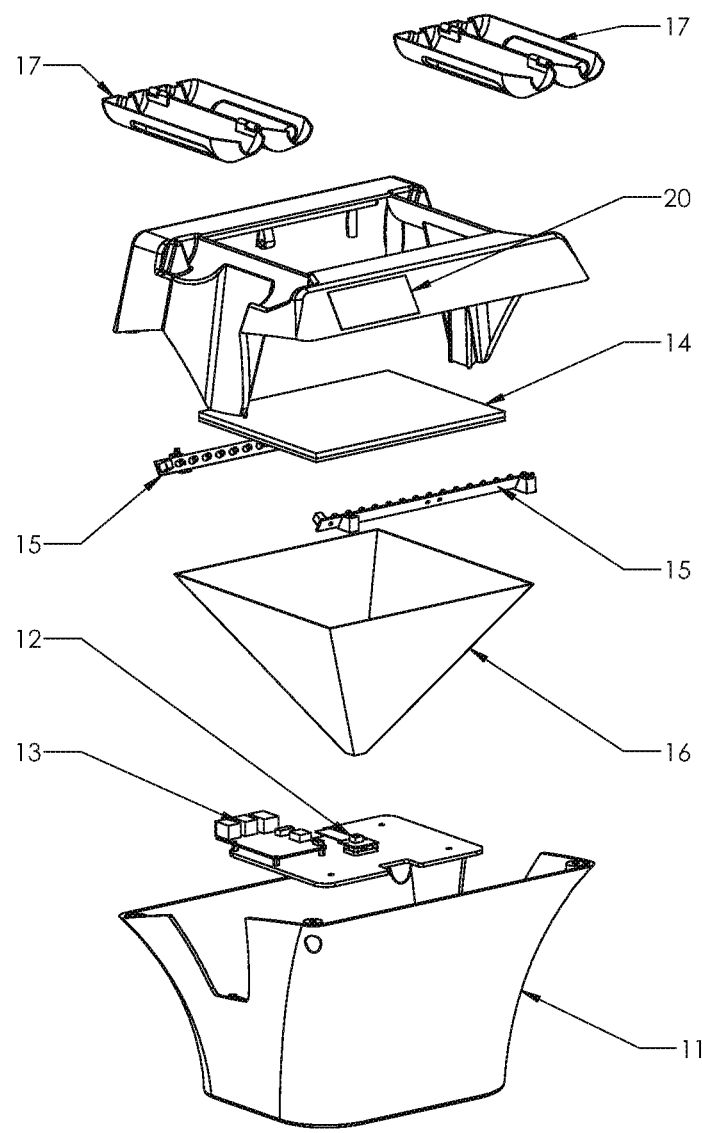
FIG. 1 illustrates an exploded view of one embodiment of a visual counting system.

In a preferred embodiment, the device 10 consists of a housing 11 with an upper counting surface 14. The housing 11 houses a camera 12, a light source 15, and an image processor or computer 13, these components being located beneath the counting surface 14. Pills or small items to be counted are poured onto the counting surface 14 and illuminated from below via the light source 15. The light bounces off the pills, reflecting back the camera 12 which captures an image. The computer 13 runs an algorithm which calculates the number of pills on the counting surface 14.

FIG. 1 illustrates an exploded view of a preferred embodiment of the present invention. Within the housing 11, there is a camera 12 and computer 13 capable of processing the images taken by the camera 12. The computer 13 may also be programmed to interface with pharmacy management systems, this capability being explained in further detail herein. The camera 12 may be mounted in any desired location within the housing 11 and any desired distance from the counting surface 14, provided the camera 12 is positioned below the counting surface 14. However, in a preferred embodiment, the camera 12 is centered at the bottom of the housing 11, approximately 8 inches below the counting surface 14, and may have a preferably cone or pyramid-shaped shield 16 surrounding the camera 12 and projecting upward toward the counting surface 14, the shield 16 preferably terminating just below the light source 15 (see FIGS. 1 and 3b). This shield 16 helps to reduce background reflection and glare that may otherwise be picked up by the camera 12 during image processing, thereby providing a clearer, more accurate image of the pills or items to be counted. It is also preferred that the camera 12 not have the standard IR filter commonly found on cameras, thus retaining the capability of capturing an image from an IR light source.

The computer 13 uses an algorithm to calculate how many pills are present on the counting surface 14. The algorithm takes into account different sizes, shapes, and color patterns of pills, tablets, capsules, etc., as well as the fact that a number of pills may clump or cluster together on the counting surface 14. The computer 13 can also have an addition feature for adding more than one counted image together in the event that one needs to count more pills than what will fit on the surface 14 at one time. In a more basic, cost-efficient system, the computer 13 may be programmed mainly to count and display the number of pills. In a higher-end, more complex version, the computer 13 may also be able to determine recommended vial size; capture, save, and transmit images; and help maintain pill inventory. The system 10 can operate as a stand-alone device or may be connected to other networks, terminals, and/or interfaced with pharmacy management systems. Interfacing with pharmacy management systems allows the images to be linked to specific patient prescription records and pharmacy inventory.

Figure 3A:
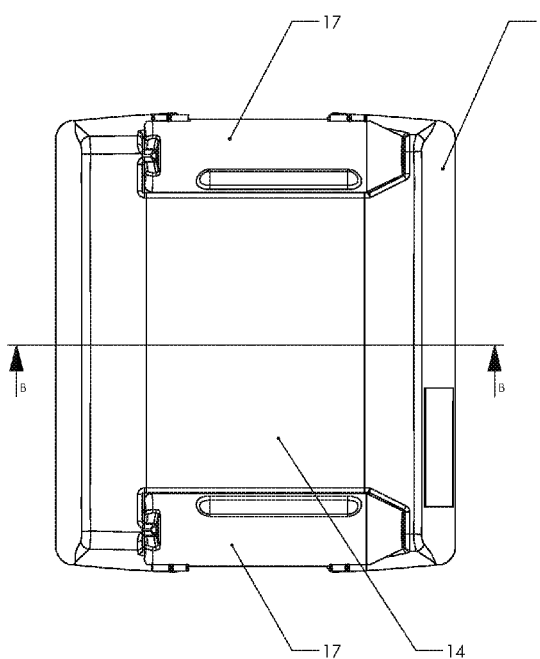
FIG. 3a illustrates a top view of one embodiment of a visual counting system with two pill chutes in a closed position.
Figure 3B:
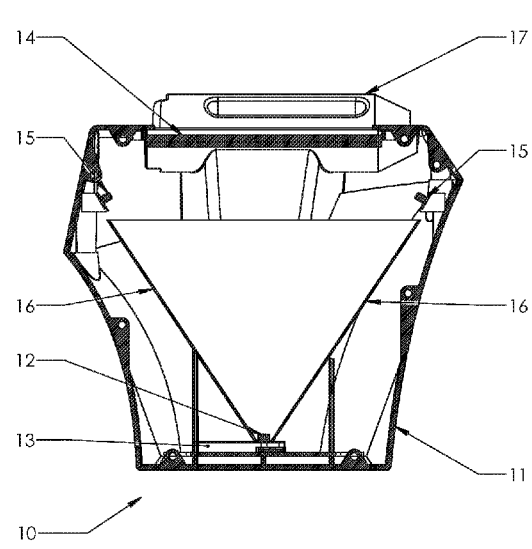
FIG. 3b illustrates a cross-sectional view of one embodiment of a visual counting system.

The light source 15 may be a portable, cost-efficient light source such as IR emitting LED lights; although, any suitable light source may be utilized. The quantity and positioning of the light source 15 may vary as desired or needed; however, optimal placement of the lights is preferred for reducing glare when capturing an image. In a preferred arrangement, multiple IR emitting LED lights 15 may be connected in circuit and mounted or attached to an upper portion of a side (or sides) of the interior of the housing 11, as shown in FIG. 3b. For example, an array of 25 IR LED lights may be connected in circuit, forming a single line or strip of LED lights that may mounted along an upper portion of the longer dimension of the housing 11, approximately 2 inches below the counting surface 14; another 25 lights may be mounted on the opposite, upper side of the housing 11, resulting in 50 lights total. Positioning the light source 15 on a side of the housing 11 near the top of the housing 11, rather than at or near the floor of the housing 11, helps focus and direct more light toward the counting surface 14 while reducing the amount of light that may reflect off the interior of the housing 11 and its components.

The upper counting surface 14 may be constructed of any suitable material such as glass, plastic, acrylic, or any other suitable material. However, in a preferred embodiment, the counting surface 14 is constructed of a dark material that allows the transmission of IR light, such as a tinted IR transmissive plastic. The counting surface 14 may be designed in any desired dimension, although a preferred dimension is approximately 6 inches by 8 inches. In typical pill counting devices, a light source shines from below a counting surface, while a camera placed above the counting surface captures an image, resulting in the image displaying the pills as a black silhouette with a white background. With the pill counting device 10 of the present invention, both the light source 15 and the camera 12 are below the counting surface 14, resulting in the pills being displayed as white or lighter in color against a darker background. By using a dark or tinted counting surface 14, the contrast of the pills to background is enhanced, resulting in a better image.

Figure 2:
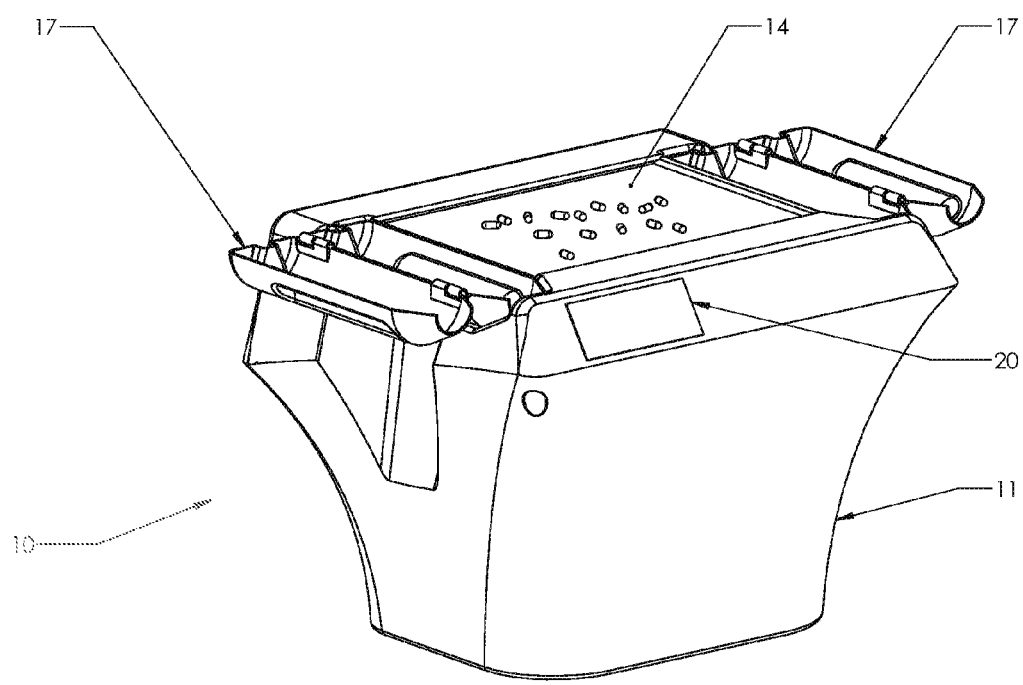
FIG. 2 illustrates a perspective view of one embodiment of a visual counting system with pills present on the counting surface and two removable pill chutes in an open position.

The counting surface 14 may be mounted in an upper portion or upper surface of the housing 11. An upper portion of the housing 11 may include a digital touch screen. LCD display, or another suitable type of display 20, as best shown in FIG. 2, for displaying the number of pills on the counting surface, error messages, and any other useful and desired information. This display 20 may include buttons for clearing the count, saving the current count, scrolling through menu functions, etc. The housing 11 may also include a barcode scanner for barcode verification of prescriptions and linking such to pharmacy management systems.

Figure 4:
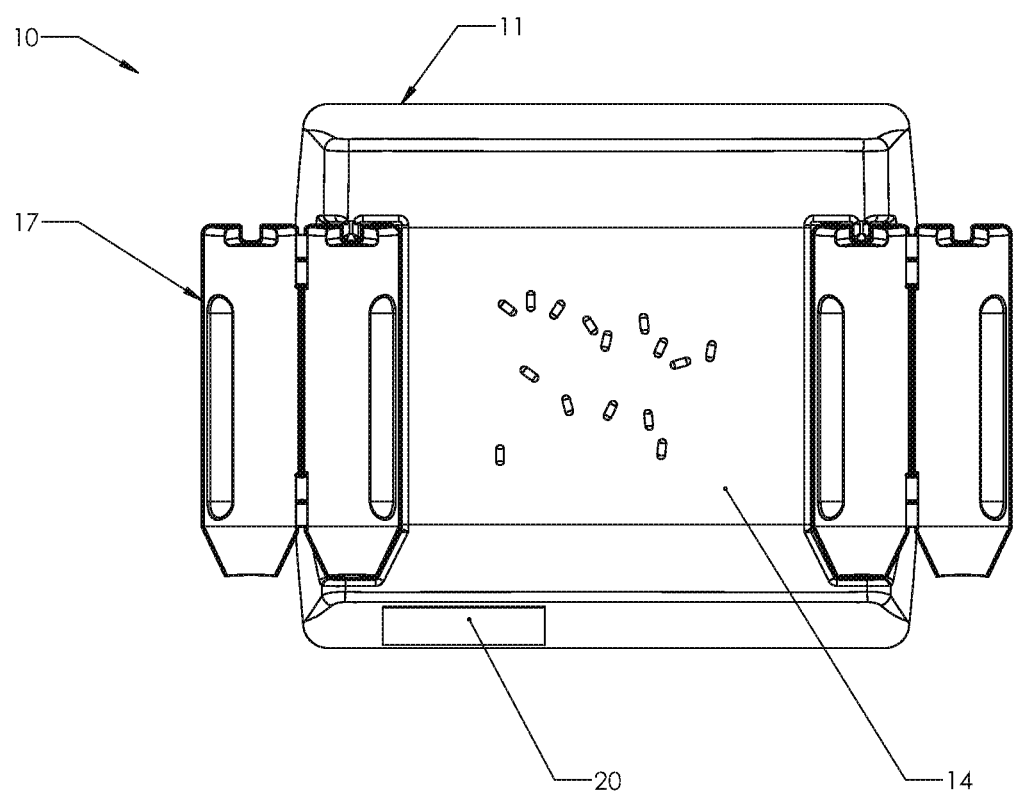
FIG. 4 illustrates a top view of one embodiment of a visual counting system with pills present on the counting surface and two removable pill chutes in an open position.

Removing the pills from the counting surface 14 may be accomplished in a number of ways. In one embodiment, at least one removable receptacle 17 or pill chute—preferably two—may be present on the upper or top portion of the housing 11, located adjacent to the counting surface 14, as shown in FIGS. 2-4. In a preferred embodiment, the pill chute(s) 17 are cylindrical shaped and hinged on one side such that the upper portion of the chute 17 may be opened, preferably away from the counting surface 14 (as shown in FIG. 2), and pills may be swiped, either by hand, spatula or another method, into the pill chute 17. The chute 17 is preferably funnel or cone-shaped on one end, as shown in FIGS. 3a and 4, such that pills may slid easily from the pill chute 17 directly into a vial or container. It is contemplated that the pills may be swiped into an open pill chute 17, the chute 17 may then be closed and removed from the counting surface 14, and the pills may be poured from the chute 17 into a vial or bottle for prescription filling or restocking.

The removable receptacle 17 or pill chute may be any suitable size, and it is contemplated that the system 10 may be designed to accommodate a number of different sized chutes. For example, a smaller chute may be used when counting a smaller number of pills; the smaller chute then being removed and replaced with a larger chute for counting a larger number of pills. This larger chute may be more bucket shaped, capable of snapping or fitting in place of the smaller chute, but having more overhang off the side of the housing for collecting a larger quantity of inventory.

Figure 5:
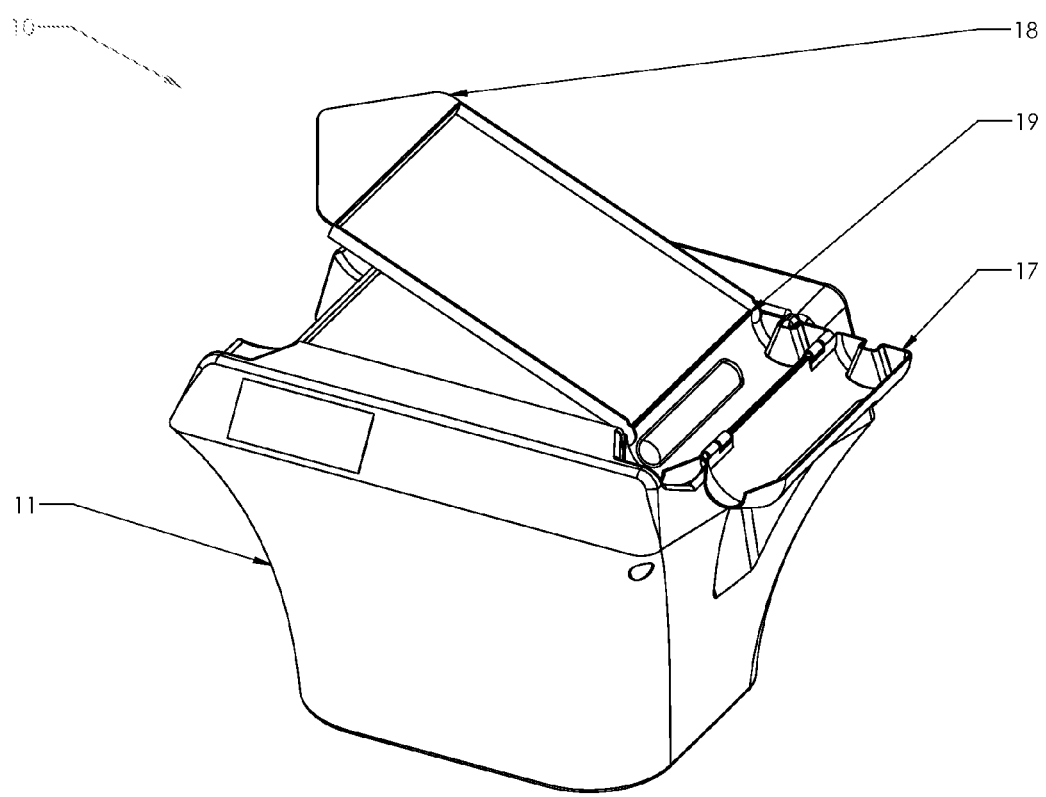
FIG. 5 illustrates a perspective view of one embodiment of a visual pill counting system with a hinged tray for pill removal.

In an alternative embodiment, the counting surface 14 and entire upper portion of the housing 11 may act as a flip tray with a handle 18 on one side and a removable pill chute 17 on the other, such that the entire upper surface of the housing 11 may be flipped up using hinged means 19, similar to a copy machine or scanner, so that the pills slid down into the pill chute 17, as shown in FIG. 5. In this way, the pills are not actually touched, and the counting surface 14 is better preserved from scratches that may otherwise result from physically swiping the pills off the counting surface 14 with a spatula or other means. The pill chute 17 may then be closed and removed from the housing so that the pills may be poured from the chute 17 into a vial or bottle.

In yet another embodiment, the upper surface of the housing 11 may be removable, similar to the count-and-pour tray systems widely used in pharmacies. In this embodiment, the entire counting surface 14 may be removed from the housing, picked up, and tilted to pour the pills into a counting pod, pill chute, or other receptacle.

In the event that the interior of the housing 11 may need to be accessed, such as for maintenance or repair, an access panel may be provided. This access panel may be hinged, snapped, or inserted in place by any suitable mechanism such that the panel may be opened or removed, thereby providing access to the interior of the housing 11 and device 10 components.

To use the visual counting system 10 of the present invention, a user may pour an undetermined number of pills on the upper counting surface 14. The pills are illuminated from below by a light source 15 present underneath the counting surface 14. The light reflects off the bottom of the pills while passing through any empty space on the counting surface 14, resulting in a light/dark contrast of pills to background. The resulting image is captured by the camera 12 which is mounted below the counting surface 14, while any extraneous reflection or glare may be minimized by a shield 16 projecting up from the camera 12. A computer 13 or image processor calculates the number of pills in real time, as well as any additional information which can then be displayed on a screen 16 that may be present on the housing 11 of the counting system 10. The user may adjust the number of pills on the counting surface 14 in order to reach the desired number on the display 20. Once counting is complete, the user may slide or swipe the pills from the counting surface 14 into a pill chute, vial, or other receptacle 17. While this description is a more simplified version of using the present invention, the process may include additional or more complex steps depending on the particular features provided by different embodiments disclosed herein.

While the spirit of the invention has been described in detail with reference to particular embodiments and dimensions, the embodiments are for illustrative purposes only and do not limit the invention. It is to be appreciated that those skilled in the art can change or modify the embodiments without departing from the scope and spirit of the invention. It is to be understood that the inventive concept is not to be considered limited to the constructions and dimensions disclosed herein.

The terms used in the present application are merely used to describe particular embodiments, and are not intended to limit the present invention. An expression used in the singular encompasses the expression of the plural, unless it has a clearly different meaning in the context. In the present application, it is to be understood that the terms such as "including" or "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

What is claimed is:
1. A visual counting system comprising:
    a housing having a bottom member, four sides extending up from said bottom member, and a top member;
    a counting surface mounted within said top member of said housing such that light may be transmitted through the counting surface;

at least one removable receptacle for receiving and retaining items from said counting surface attached to said top member of said housing and positioned adjacent to at least one side of said counting surface such that items may slide from said counting surface into said receptacle for temporary placement, so that items may be contained within said removable receptacle after said receptacle is removed from said housing;

an imaging means positioned within said housing, disposed underneath and facing upwardly toward said counting surface for receiving light reflecting off of items disposed on said counting surface;

an infrared light source positioned within said housing and disposed underneath said counting surface; and an image processing means operably connected to said imaging means for counting items placed onto said counting surface.

2. The visual counting system of claim 1, whereby said counting surface is constructed from a tinted material selected from the group consisting of plastic, glass, and acrylic.

3. The visual counting system of claim 2, whereby said counting surface is constructed from a material capable of transmitting infrared light and opaque to visible light.

4. The visual counting system of claim 1, wherein said light source comprises two strips of infrared emitting LEDs and said strips are disposed along opposing sides of said housing.

5. The visual counting system of claim 1, whereby said receptacle is generally cylindrical shaped and one end is generally funnel shaped, said receptacle further including a hinge means disposed longitudinally along said receptacle between opposing ends such that said receptacle may be opened and closed.

6. The visual counting system of claim 1, whereby said receptacle is a generally bucket shaped to hold a larger quantity of counted items.

7. The visual counting system of claim 1, whereby said top member further includes a hinge means along one side and a handle along an opposite side, allowing the top member to be tilted upwards for clearing items from said counting surface.

8. The visual counting system of claim 7, wherein said receptacle is attached to said hinged means of said top member, such that as the top member is tilted upwards, items may slide off said counting surface and into said receptacle.

9. The visual counting system of claim 1, further including a barcode scanner operatively connected to said image processing means.

10. The visual counting system of claim 1, whereby said system is operatively connected to a pharmacy management system.

11. The visual counting system of claim 1, further including a shielding means disposed about said imaging means and projecting upward toward said counting surface.

12. A method of counting pills comprising the steps of:
providing a layered counting surface opaque to visible light that comprises a layer capable of transmitting infrared light disposed adjacent to a glass layer;
providing an infrared light source, an imaging means, and an image processing means disposed underneath said counting surface;
placing a plurality of pills on said counting surface;
transmitting infrared light through said counting surface to illuminate said pills from below said counting surface;
using said imaging means to capture infrared light reflected back through said counting surface off pills positioned on said counting surface;
processing said captured infrared light with said image processing means; and
determining the number of pills on said counting surface.

13. The method of claim 12, further including the step of enclosing said infrared light source, said imaging means, and said image processor within a housing.

14. The method of claim 12, wherein said infrared light source comprises two strips of infrared emitting LEDs and said strips are disposed along opposing sides of said counting surface.

15. The method of claim 12, further including the steps of:
providing a removable receptacle for receiving and containing pills from said counting surface after said receptacle has been removed from said counting surface; and
transferring said pills from said counting surface to said removable receptacle for temporary placement.

16. The method of claim 12, further including the step of connecting said image processing means to a pharmacy management system.

17. The method of claim 12, further including the step of shielding said imaging means to reduce background reflection.

* * * * *